(12) United States Patent
Muller et al.

(10) Patent No.: US 9,819,074 B2
(45) Date of Patent: Nov. 14, 2017

(54) MONOLITHICALLY INTEGRATED IMPLANTABLE FLEXIBLE ANTENNA FOR ELECTROCORTICOGRAPHY AND RELATED BIOTELEMETRY DEVICES

(71) Applicant: THE REGENTS OF THE UNIVERSITY OF CALIFORNIA, Oakland, CA (US)

(72) Inventors: Rikky Muller, Kirkland, WA (US); Peter Ledochowitsch, Kensington, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 823 days.

(21) Appl. No.: 14/205,336

(22) Filed: Mar. 11, 2014

(65) Prior Publication Data
US 2014/0257052 A1   Sep. 11, 2014

Related U.S. Application Data

(60) Provisional application No. 61/776,416, filed on Mar. 11, 2013.

(51) Int. Cl.
*H01Q 7/00* (2006.01)
*A61B 5/00* (2006.01)
(Continued)

(52) U.S. Cl.
CPC .............. *H01Q 1/273* (2013.01); *A61B 5/002* (2013.01); *A61B 5/0031* (2013.01);
(Continued)

(58) Field of Classification Search
CPC .............. A61B 5/04001; A61B 5/6868; A61B 2562/028; A61B 5/002; A61B 5/0031; H01Q 1/273; H01Q 1/2225; H01Q 7/00
(Continued)

(56) References Cited

U.S. PATENT DOCUMENTS

| 8,343,068 B2* | 1/2013 | Najafi | A61B 5/0031 600/561 |
| 8,849,369 B2* | 9/2014 | Cogan | A61B 5/0006 600/378 |

(Continued)

OTHER PUBLICATIONS

Bjorninen, T., "Design of Wireless Links to Implanted Brain-Machine Interface Microelectronic Systems," Antennas and Wireless Propagation Letters, IEEE , vol. PP, No. 99, pp. 1-4 (Dec. 2012).

(Continued)

*Primary Examiner* — Tho G Phan
(74) *Attorney, Agent, or Firm* — O'Banion & Ritchey LLP; John P. O'Banion

(57) ABSTRACT

A sub-skin-depth (nanoscale metallization) thin film antenna is shown that is monolithically integrated with an array of neural recording electrodes on a flexible polymer substrate. The structure is intended for long-term biometric data and power transfer such as electrocorticographic neural recording in a wireless brain-machine interface system. The system includes a microfabricated thin-film electrode array and a loop antenna patterned in the same microfabrication process, on the same or on separate conductor layers designed to be bonded to an ultra-low power ASIC.

18 Claims, 8 Drawing Sheets

(51) Int. Cl.
H01Q 1/27 (2006.01)
A61B 5/04 (2006.01)
H01Q 1/22 (2006.01)

(52) U.S. Cl.
CPC ........ *A61B 5/04001* (2013.01); *A61B 5/6868* (2013.01); *H01Q 1/2225* (2013.01); *H01Q 7/00* (2013.01); *A61B 2562/028* (2013.01)

(58) Field of Classification Search
USPC .......... 343/700 MS, 718; 600/301, 372, 373, 600/508, 561
See application file for complete search history.

(56) References Cited

U.S. PATENT DOCUMENTS

| | | | |
|---|---|---|---|
| 9,504,177 B2 * | 11/2016 | Shah | A61B 5/6861 |
| 2007/0138010 A1 * | 6/2007 | Ajayan | G01L 1/005 |
| | | | 204/400 |
| 2009/0005656 A1 * | 1/2009 | Najafi | A61B 5/686 |
| | | | 600/301 |
| 2010/0298895 A1 * | 11/2010 | Ghaffari | A61B 1/00082 |
| | | | 607/3 |

OTHER PUBLICATIONS

Bjorninen, T., "Antenna design for wireless electrocorticography," Antennas and Propagation Society International Symposium (APSURSI), 2012 IEEE , vol., No., pp. 1-2, 8-14 (Jul. 2012).

* cited by examiner

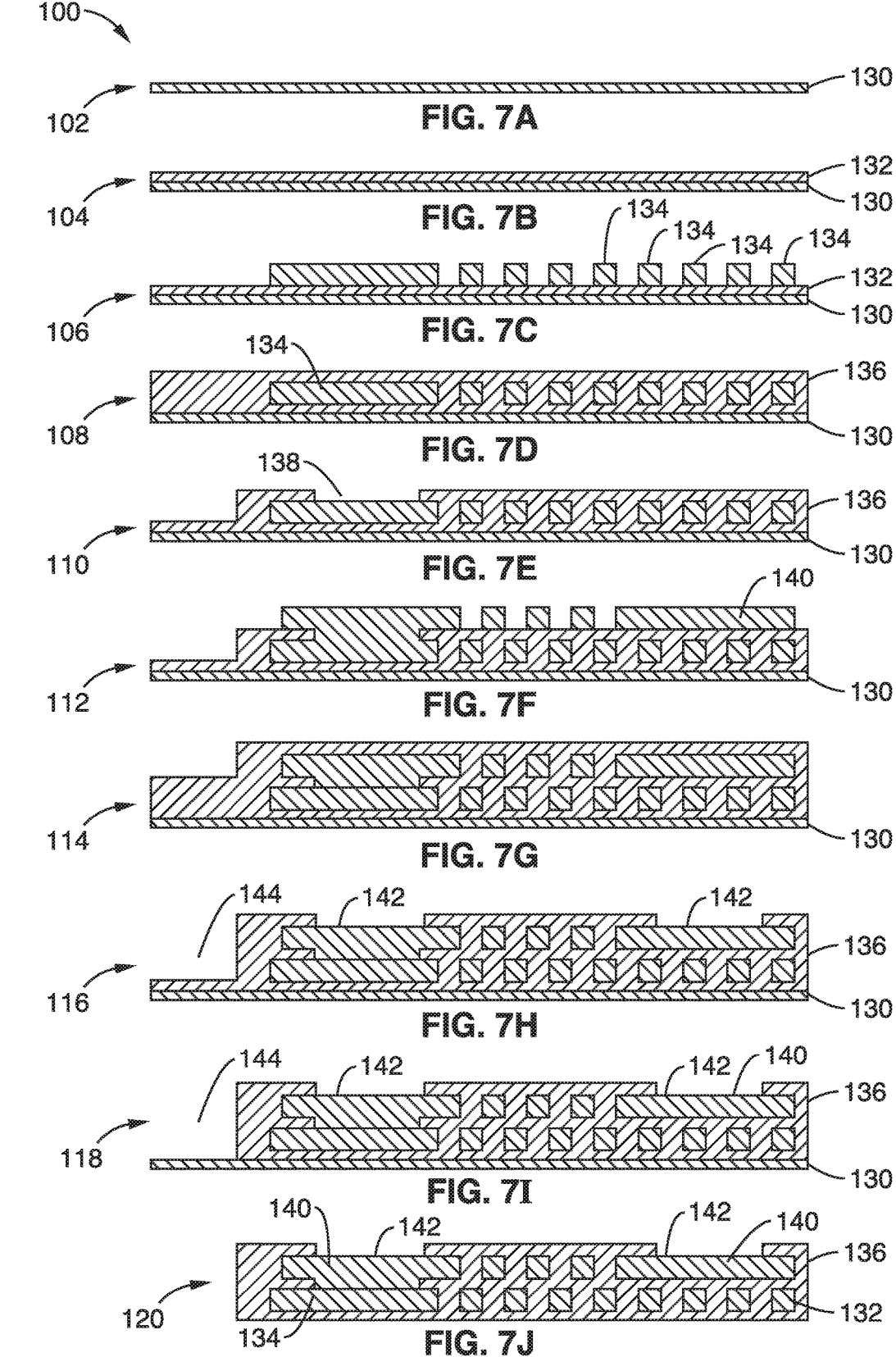

MONOLITHICALLY INTEGRATED IMPLANTABLE FLEXIBLE ANTENNA FOR ELECTROCORTICOGRAPHY AND RELATED BIOTELEMETRY DEVICES

CROSS-REFERENCE TO RELATED APPLICATIONS

This application claims the benefit of U.S. provisional patent application Ser. No. 61/776,416 filed on Mar. 11, 2013, incorporated herein by reference in its entirety.

STATEMENT REGARDING FEDERALLY SPONSORED RESEARCH OR DEVELOPMENT

Not Applicable

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally to an implantable sensor system, and more particularly to an implantable sensor with integrated antenna.

2. Description of Related Art

Recent advances in the field of brain-machine interfaces (BMI) have caught wide attention in engineering and medicine. Wireless brain-machine interface (BMI) systems fit for long-term neural recordings during patients' normal activities may aid in the diagnosing of diseases, such as epilepsy, sleep and mental disorders (pertinent examples, non-exclusively: obsessive-compulsive disorder, deep depression, Parkinson's Disease). Moreover, this technology holds therapeutic promise to restore mobility and communication for patients suffering from spinal cord injuries and neurodegenerative diseases (e.g. ALS, other forms of locked-in syndrome) by enabling direct brain-control of prosthetics (motor, communication, etc.).

However, current solutions for implantable antennas generally require rigid substrates such as printed circuit boards and hermetic sealing, leading to un-economically large footprint and height for the electronics. Furthermore, wired readout of neural activity poses a high infection risk and is hence only fit for short-term clinical use.

Battery-powered systems require perilous and expensive surgeries for replacing the discharged batteries. Thus, achieving fully wireless and battery-free operation is presently a major focus in the field of implantable neural hardware.

State of the art work on implantable antennas for BMIs has been focused on antenna miniaturization in order to minimize tissue scarring and immune response to the implant. However, this extreme miniaturization has been at the expense of link power efficiency, which drops sharply as the implant size is reduced below a few millimeters.

BRIEF SUMMARY OF THE INVENTION

An aspect of the present invention is a thin film antenna, monolithically integrated with an array of neural recording electrodes on a flexible polymer substrate. The structure is intended for long-term biometric data and power transfer such as but not limited to electrocorticographic neural recording in a wireless brain-machine interface system. The system comprises a microfabricated thin-film electrode array and a loop antenna patterned in the same microfabrication process, on the same or on a separate conductor layer. Fabricating the antenna together with the electrodes provides a small form factor, mechanical flexibility of the structure and minimal cabling to the active circuits enabling seamless integration of all electronic components.

Another aspect is an antenna that can serve as the wireless link of a battery-free BMI microelectronic system based on electrocorticography (ECoG) as well as related implants that require external data transfer and power delivery.

Another aspect is a wireless brain-machine interface (BMI) implant having the following components monolithically integrated within the same flexible substrate: (a) electrodes for neural signal acquisition; (b) active electronics to amplify, process and transmit the signal; and (c) an antenna for power delivery and data transmission between the implant and an external reader.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIG. 7A through FIG. 7J show a schematic cross-sectional diagram of a step-by-step wafer-level fabrication process suitable for manufacturing an integrated antenna/array device with single or multiple layers in accordance with the present invention.

DETAILED DESCRIPTION OF THE INVENTION

Figure 1:
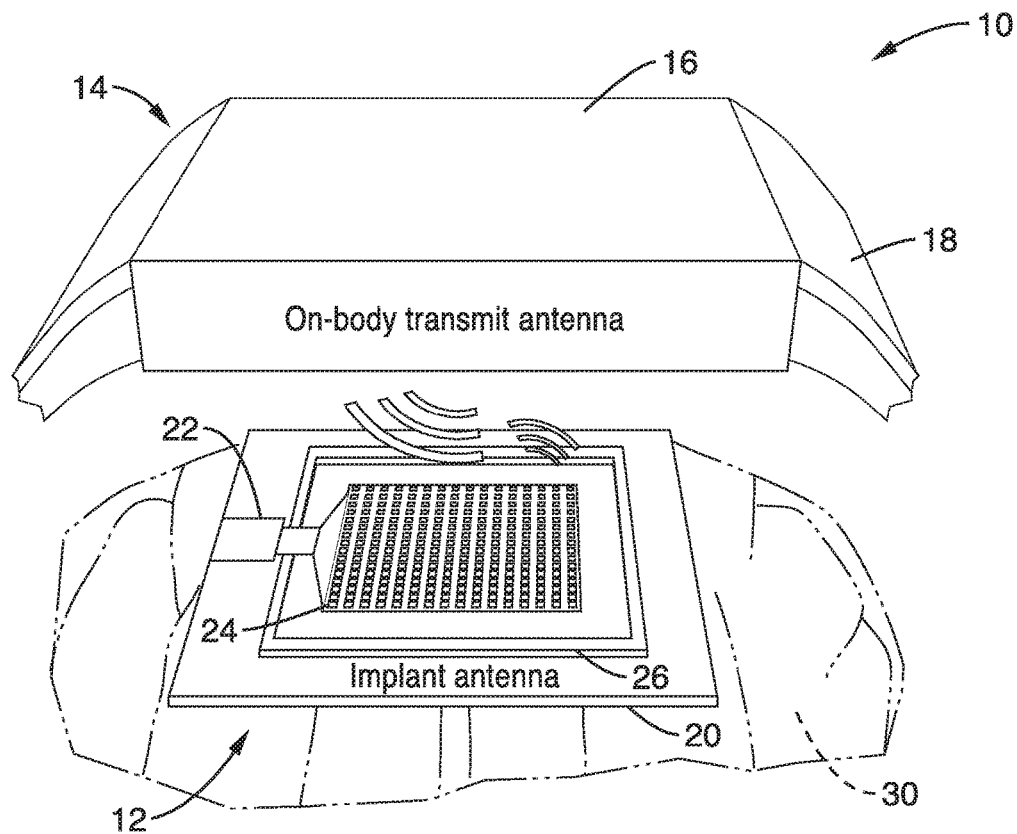
FIG. 1 is a schematic view of wireless brain-machine interface (BMI) system comprising a wireless implant and external reader in accordance with the present invention.

FIG. 1 is a schematic view of wireless brain-machine interface (BMI) system 10 comprising a wireless implant 12 and external reader 14 in accordance with the present invention. The implant 12 generally comprises the following components monolithically integrated onto or within the same flexible substrate 20: (a) an array of one or more electrodes 24 for the acquisition of bioelectric (e.g. neural) signals; (b) active electronics/circuitry 22 to amplify, process and transmit signals relating to one or more physiological characteristics of the patient; and (c) an antenna 26 for power delivery and data transmission between the implant 12 disposed within tissue 30 of body of a patient and the external reader 14 located external to the patient.

Thus, the electrode array 24 circuitry 22 and antenna 26 all form one monolithically integrated device. For purposes of this description, a "monolithically integrated device" is herein defined as a device having components that are intractably and/or functionally indivisible from each other and formed on or from the same substrate, or sharing a substrate to form a unitary cooperating circuit, or were fabricated simultaneously in the same wafer-level cleanroom fabrication process.

In a preferred embodiment, the external reader 14 may generally comprise an on-body transmitting/receiving antenna 16 that is externally coupled to the patient via attachment means 18. It is appreciated that external reader 14 may also be located at differing locations in proximity to the patient.

According to a preferred embodiment of the present invention, the antenna 26 and implant 12 are configured to function as the wireless link of a battery-free BMI microelectronic system based on electrocorticography (ECoG). ECoG is a neural recording technique where an array of electrodes is placed on the surface of the cerebral cortex to record the aggregate electrical activity of postsynaptic potentials generated by ensembles of cortical neurons. In such embodiment, implant 12 comprises a high-density microfabricated ECoG grid 24 and a loop antenna 26 and associated electronics 22 bonded/fabricated as an integrated circuit to perform signal acquisition, wireless power delivery and communication within the skull of a patient.

Figure 2:
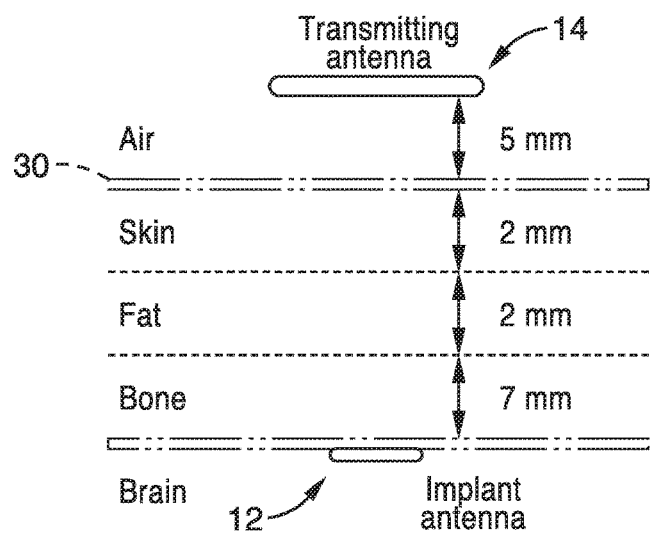
FIG. 2 shows a schematic system side view of the implant used in cooperation with external antenna and intervening media/anatomy.
Figure 3:
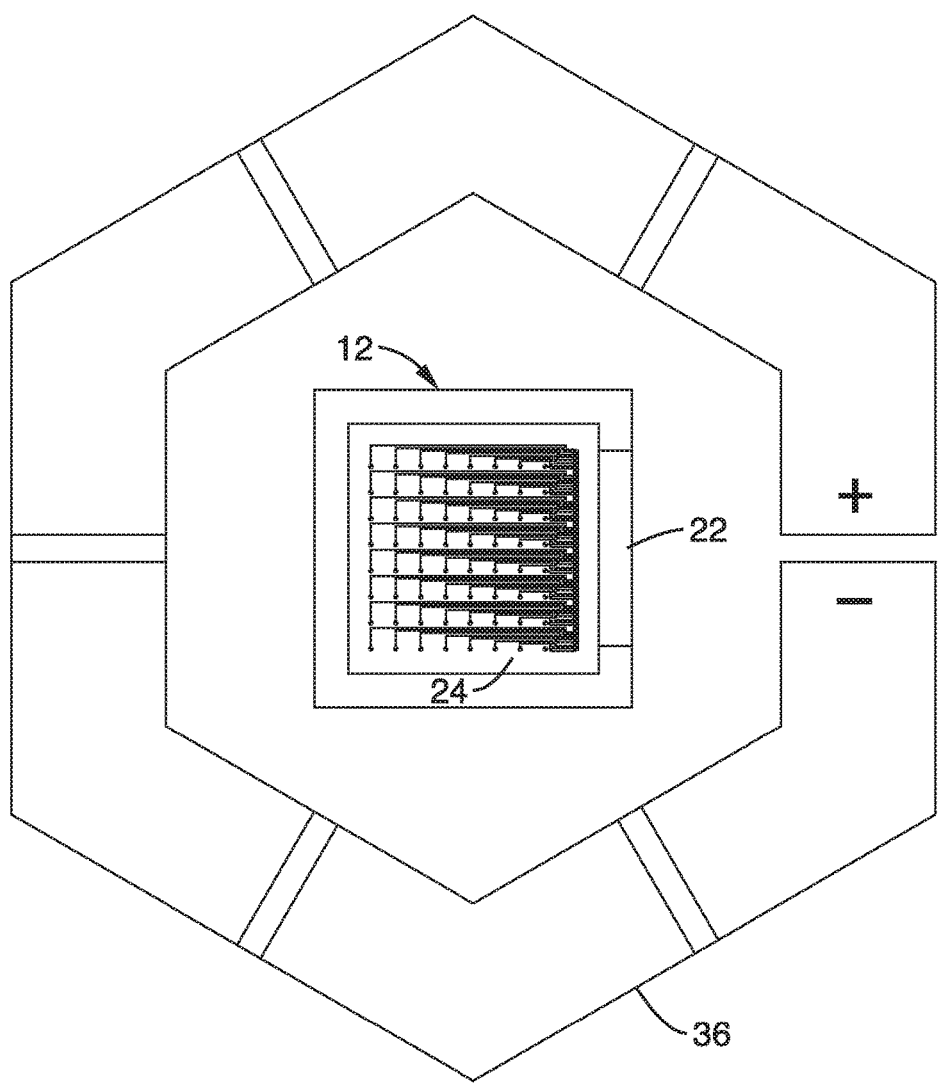
FIG. 3 is a plan view of the implant FIG. 2.
Figure 4:
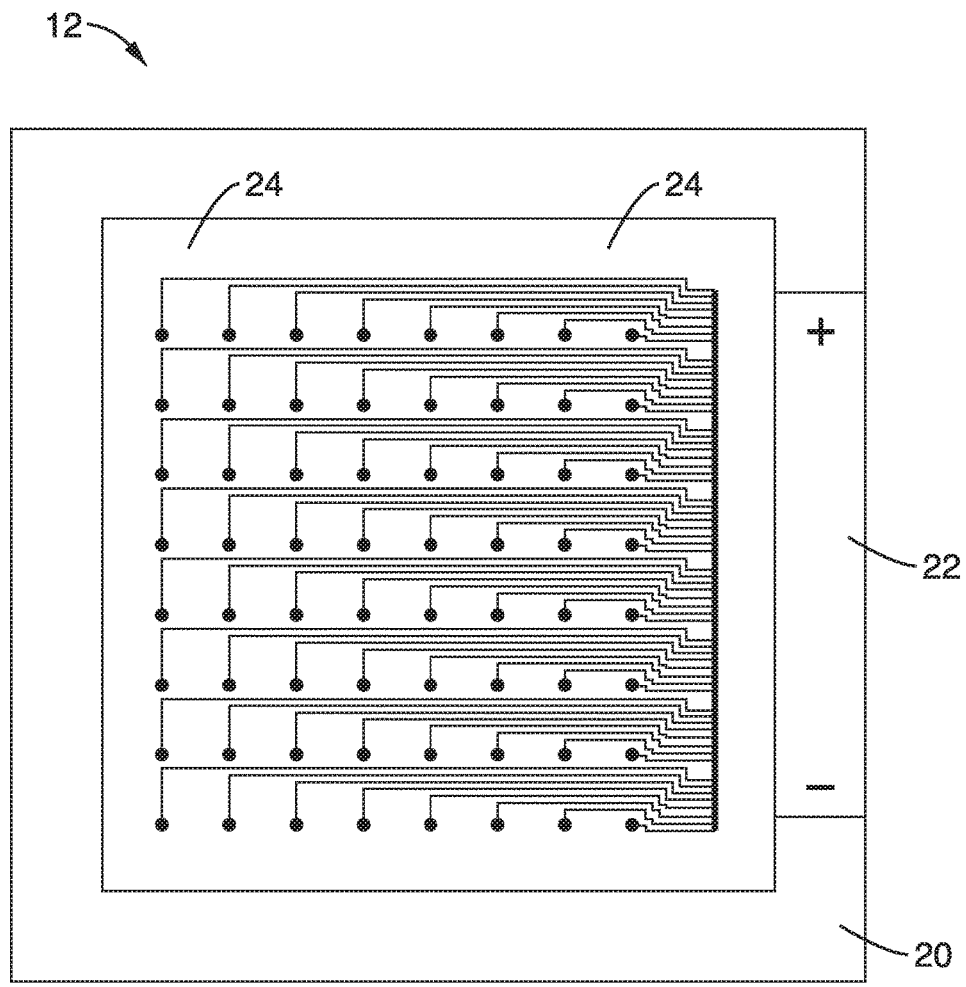
FIG. 4 shows a close-up view of the implant of FIG. 3.

FIG. 2 shows a schematic system side view of the implant 12 of FIG. 3 and FIG. 4 used in cooperation with external antenna 14 and intervening media/anatomy. As shown in FIG. 2, the transmitting antenna may be located above (e.g. 5 mm gap) the skin of the patient's tissue 30. This gap, along with the thickness of the skin (2 mm), fat (2 mm) and bone (7 mm) generally separate the external antenna 14 from the implant 12, which is implanted at the surface of the cerebral cortex underneath the skull of the patient. As shown in the top or plan view of the system 10 in FIG. 3, the external antenna 16 is segmented into segments 16 using capacitors to render the current distribution along the loop uniform. The capacitors that couple the segments 36 counteract the phase shift along the electrically large loop. Each segment 36 is short compared to the effective carrier wavelength and each capacitor resonates out the inductance of the loop divided by the number of segments 36. The segmented antenna 16 helps to couple more power into the implant without exceeding Federal Communications Commission' (FCC) safety limits on the specific absorption ration (SAR).

FIG. 4 shows a close-up view of the implant 12, along with electrode array 24 and microchip circuitry/electronics 22 on substrate 20.

FIG. 2 through FIG. 4 illustrate one possible variation of antenna topology in accordance with the present invention. Multi-layer metal enables antenna 26 geometries where the presence of the antenna does not consume additional substrate 20 area beyond what is required to define the sensor 24. A multi-loop antenna (not shown) can be fabricated with a multi-layer metal process as well.

The implant 12 of the present invention overcomes two main challenges faced in configuring a practical integrated system for ECoG implantation, including: 1) integration of the components together in a hermetically sealed environment with only exposure to the biological tissue at the electrode sites, and 2) structure of the components in a small form factor, particularly in the z-axis (perpendicular to the surface of the brain) in order to minimize foreign body responses such as scarring of brain tissue.

As will be explained in further detail below, the antenna 26 is micro-patterned onto a polymer thin-film 20 together with the ECoG electrodes 24, thus enabling a larger antenna size while eliminating the need to implant a large rigid structure. The nanoscale thickness of the metallization allows the entire structure of the implant 12 to be flexible and conformal. Flexibility allows the structure to conform to the curved topography of the brain (or other anatomical feature) improving signal fidelity and reducing trauma to surrounding tissues.

To allow for a trans-cranial-wireless µECoG that avoids skull-penetrating wires for data read-out and powering, the antenna 26 (which is configured for both power delivery to the implant 12 and data transmission to and from the implant) is preferably fabricated on the same flexible metal layer onto which the µECoG electrodes 24 are patterned. This design avoids the need for a large rigid structure to be implanted into the intracranial space.

Figure 5:
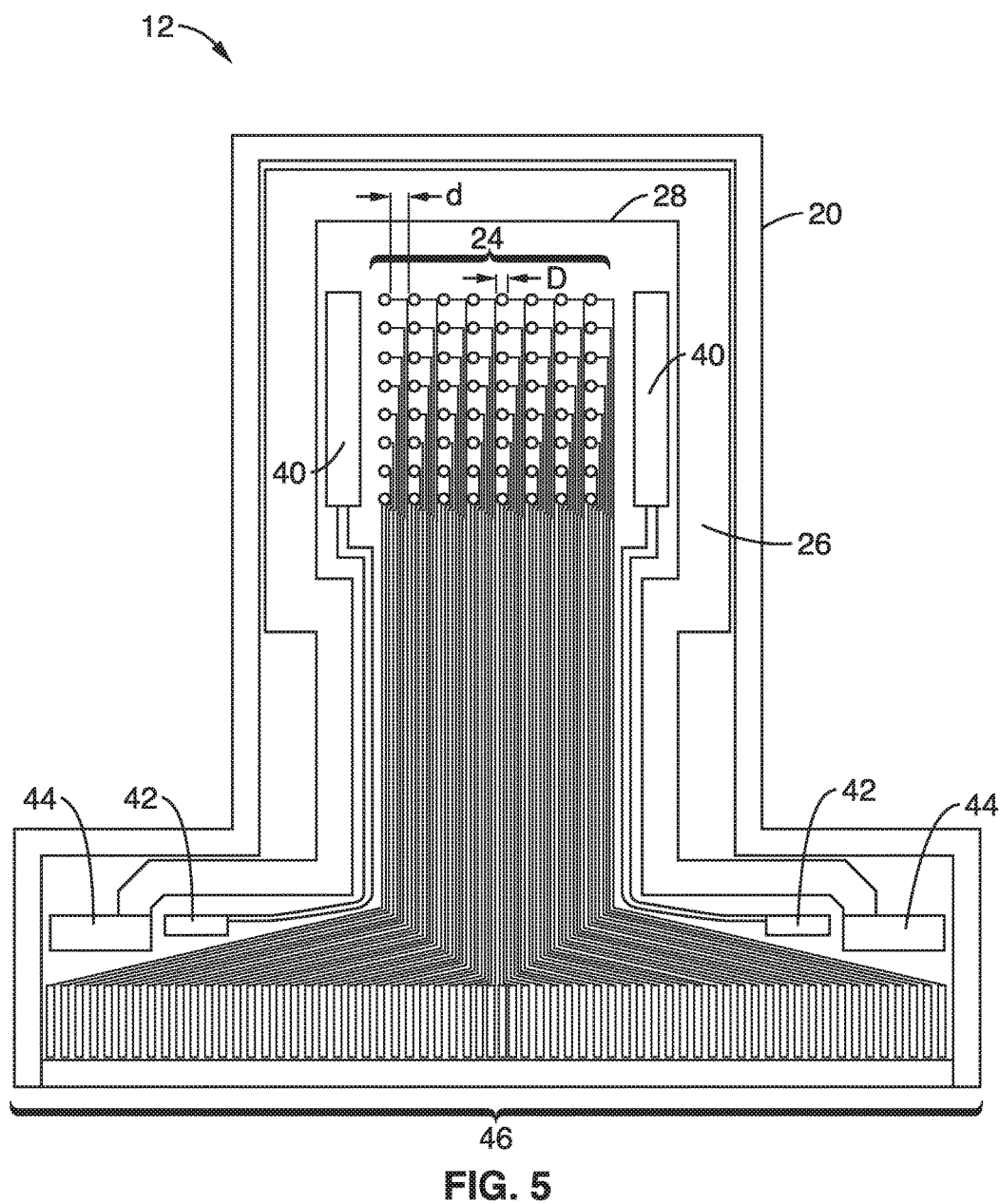
FIG. 5 illustrates a detailed schematic diagram of an antenna and µECoG electrode implant integrated as an application-specific integrated circuit (ASIC) in accordance with the present invention.

FIG. 5 illustrates a detailed schematic diagram of an antenna and µECoG electrode implant 12 integrated as an application-specific integrated circuit (ASIC) in accordance with the present invention. The overall form factor of implant 12 is configured to have a high-density µECoG array for clinical use (400 µm electrode pitch, 8×8 channels) that is large enough to provide clinical application in humans, e.g. for communication BMI (3 mm×3 mm total area of the sensor array), yet with an overall form that is small enough to be testable in rodent models (6.5 mm×6.5 mm total head size, including antenna).

Antenna 26, which resides on the same layer as array 24, comprises a square single loop antenna trace 28 (approximately 750 µm trace width), and was simulated in Ansys high frequency structural simulator (HFSS) to ensure that sufficient power can be coupled in wirelessly across the skull without exceeding the maximum specific absorption ratio (SAR) allowed by the FCC. The implant includes two internal references 40 on either side of the array 24 that effectively act as a physical common-average reference across the sensor grid 24 field of view. The total area of both references 24 preferably equals to the total area of all μECoG electrodes 24 (impedance matching) so as to reduce 60 Hz noise entering the IC front-end.

The implant also comprises a series of bond pad arrays (pads 42 for references 40, pads 44 for antenna 26, and pads 46 for electrodes 24) interconnected by thermo-compression bonding, e.g., using an anisotropic conductive film (ACF). The ACF bond pads 42, 44 for the references 40 and the antenna 26, respectively, are configured to be particularly large in area in order to ensure interconnect robustness and low impedance. In addition, the electrode 24 diameter D and the electrode 24 edge-to-edge spacing d obey the "Spatial Nyquist" condition D>d/2, i.e. they act as a spatial anti-aliasing filter to provide consistent spatial (spectral) pattern analysis of ECoG activity.

Figure 6A:
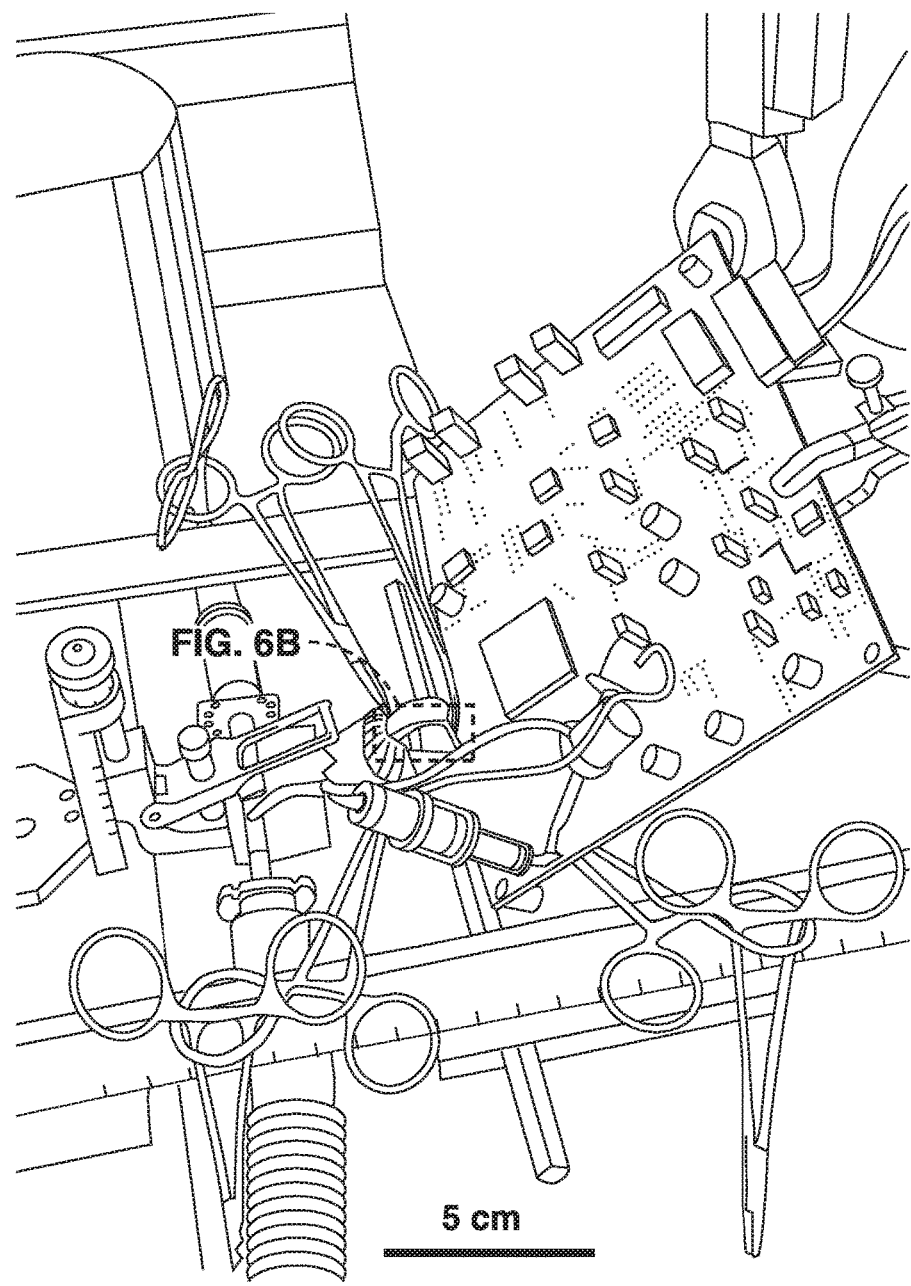
FIG. 6A is a photo of the overall procedure setup for testing the antenna implant of the present invention.
Figure 6B:
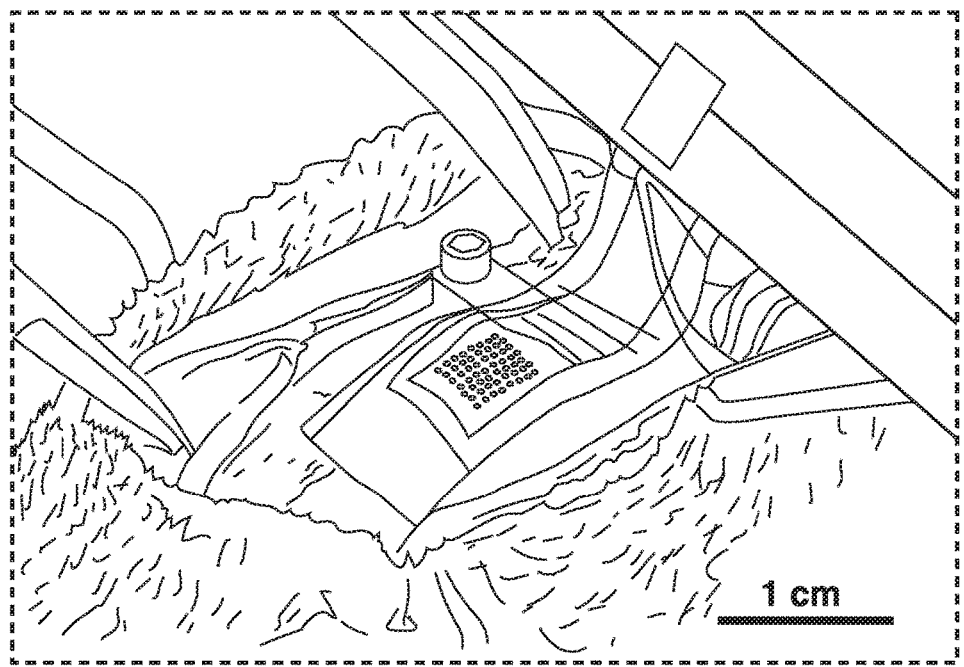
FIG. 6B is a photo showing a close-up view of the implant implanted over a rat cortex for testing purpose.
Figure 6C:
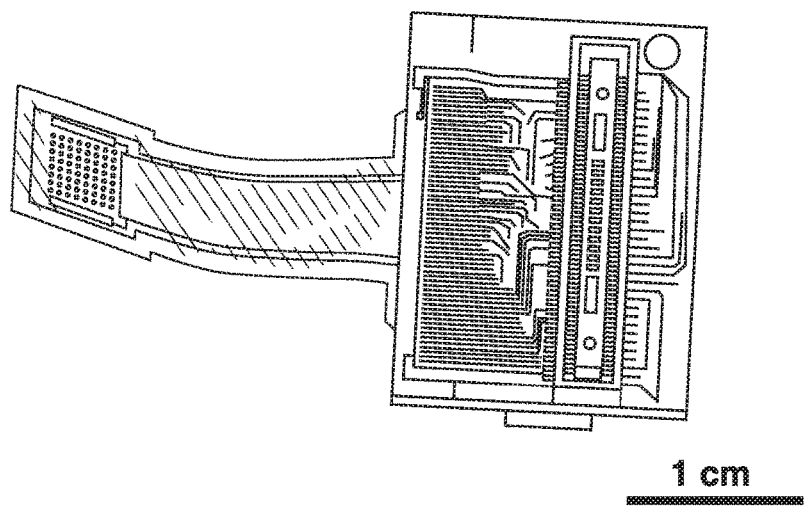
FIG. 6C is a photo showing an implant comprising a µECoG array with monolithically integrated antenna ACF-bonded to a controlled-impedance adapter board.

The implant 12 (ASIC in conjunction with the Parylene C μECoG array 24) was successfully bench and in vivo tested. FIG. 6A through FIG. 6C show photographs of the testing setup used. FIG. 6A is photo of the overall procedure setup for testing the antenna implant 12 of the present invention. FIG. 6B is a photo showing a close-up view of implant 12 implanted on a rat cortex. FIG. 6C is a photo showing implant 12 comprising an μECoG array with monolithically integrated antenna ACF-bonded to a controlled-impedance adapter board.

For recording neural signals from the cortex, the fabricated 8×8 electrode array with 400 μm electrode pitch was configured to capture the scale of individual cortical columns. The array 24 was configured to conform to the cortex and was therefore fabricated at wafer level on a flexible and biocompatible polymer substrate, Parylene C, in a novel MEMS process (described in further detail below). The total thickness of the conductive layer deposited by electron-beam evaporation was 200 nm (10 nm of platinum (Pt) adhesion layer, 140 nm of ductile gold (Au) core, 50 nm of biocompatible Pt passivation).

Minimizing device size and structural complexity was a top priority in the configuration of implant 12. Therefore, the implant antenna 26 was patterned onto the same substrate 20 in the same process as the ECoG electrodes 24. For the frequency range of hundreds of MHz to low-GHz range, this approach resulted in a conductor thickness of only a fraction of the skin depth at the carrier frequency. Therefore, additional loss due to current crowding was to be expected and, consequently, the degrees of freedom in the antenna design were greatly reduced. For instance, long and narrow antenna traces were to be avoided. A single-turn loop 28 was found to efficiently extract energy from a magnetic field and enclose the electrode array 24 to provide a single-layer structure with minimal surface area for this application. The electrode array 24 was modeled as a part of the antenna 26 to account for the EM interaction between the two.

It is appreciated that the antenna 26 geometry may be generalized. It is known in the art that multi-turn loops generally provide better performance. In the configuration illustrated, a single-turn loop 28 was chosen for simplicity of fabrication. A multi-turn loop design (not shown) may also be realized through multi-layer metal fabrication by repeating the fabrication steps illustrated in FIG. 7F through FIG. 7H. Additionally, the antenna area 26 can be scaled if increased power is demanded by the integrated circuit 22. ECoG electrodes 24 do not need to be located in the middle of the antenna 24, and may be located elsewhere on the substrate 20. However, placing the array in the center is a means for saving total area and does not cause significant interference with the antenna pattern 24.

FIG. 7A through FIG. 7J show a schematic cross-sectional diagram of a step-by-step wafer-level fabrication process 100 suitable for manufacturing an integrated antenna/array device with single or multiple layers in accordance with the present invention. At step 102 shown in FIG. 7A, a silicon carrier wafer 130 is prepped (e.g. cleaned). At step 104 shown in FIG. 7B, a Parylene C layer 132 is deposited [5 μm] on silicon carrier wafer 130. At step 106 shown in FIG. 7C, metal conductor layer 134 is formed from platinum-gold-platinum (10 nm Pt/140 nm Au/50 nm Pt) generated via e-beam evaporation and lift-off. In a preferred embodiment, metal conductor layer 134 may comprise electrode array 24, antenna loop 28, references 40 and bond pads 42, 44, and 46 all in a single layer (see FIG. 5).

At step 108 shown in FIG. 7D, Parylene C deposition [5 μm] is performed to provide an insulating layer 136 over metal conductor layer 134. At step 110 shown in FIG. 7E, vias 138 are etched in oxygen plasma. For single-layer configurations, the process is completed by performing the etch and release as illustrated in FIG. 7I and FIG. 7J. For multiple conductor layers (e.g. for multiple-loop antennas) further steps 112 through 120 in FIG. 7F through FIG. 7H may be performed repeatedly.

At step 112 shown in FIG. 7F a second conductor layer 140 (e.g. platinum-gold-platinum (10 nm Pt/140 nm Au/50 nm Pt)) is generated via e-beam evaporation and lift-off. At step 114 shown in FIG. 7G, Parylene C deposition [5 μm] is performed to build an additional insulation layer. At step 116 shown in FIG. 7H, vias 142, 144 are etched in oxygen plasma. At step 118 shown in FIG. 7I further via etch in oxygen plasma is performed. At step 120 shown in FIG. 7H the device is released from the carrier substrate 130 in mild detergent.

In one embodiment, the Parylene C layer 132 (poly-para-chloro-xylylene, obtained from Specialty Coating Systems), was conformally deposited onto the particle-free p-type silicon carrier wafer 130. Great care was taken to avoid particulate contamination of the Parylene layer 132 because such particulates may greatly reduce lithographic yield in later processing steps. The wafers 130 were taken directly out of the sealed wafer box and cleaned with a strong stream of N2. Wafers 130 were placed into a wafer cassette, also prior cleaned with nitrogen. The wafer cassette was wrapped in very fine stainless steel mesh (obtained from McNichols, square weave, stainless steel type 304, 325 mesh, 0.0014" Wire, 0.0017" opening). It was found that when deposited through the stainless steel mesh, 2.5-3 g of Parylene C dimer yielded approximately 1 μm of Parylene C on the wafer with about 10% thickness variation across the wafer. Also, the protective stainless steel mesh was not reused: Parylene deposits on the mesh and changes the pore sizes; it cannot be cleaned off easily using solvents or reactive ion etching. Total Parylene layer 132 thickness determines ultimate device stiffness and is in practice limited to approximately 8 μm per layer, which is the maximum thickness which can be etched through an 8-12 μm thick photoresist (SPR220) mask. Also, Parylene C layers must be thicker than 2 μm for insulation purposes to avoid shorts due to pinholes in the Parylene C.

The conductor 134 was patterned in a bi-layer lift-off process. All lithography masks (5", dark field, chrome on soda-lime glass) were drawn in Tanner L-Edit v14-v16 and manufactured by laser direct-write at Fineline Imaging or Frontrange Photomask. A 1.3 μm thick layer of G-line photoresist (OCG 825) was spun at 5000 revolutions per minute (RPM) onto the Parylene. The wafer was soft-baked at 90° C. for 60 seconds and flood exposed (Karl Suss MA6, 0.14 J/cm$^2$). A layer of I-line photoresist (OiR 10i 1.1 μm thick) was then spun at 4100 RPM and soft baked at 90° C. The wafer was exposed with a dose of 0.06 J/cm$^2$ and developed in OPD 4262 for 45-55 s. A 20 s etch in oxygen plasma (80 sccm and 200 W radio frequency (RF) power, process pressure≈76 mTorr) was performed in the Plasma-Therm PK-12 RIE tool to de-scum the surface and improve adhesion for metal deposition.

For conventional μECoGs with metal electrodes 24, metal conductor layers 134/140 were deposited as a tri-stack of platinum (10 nm), Au (140 nm), platinum (50 nm), obtained from Sigma-Aldrich, by electron-beam evaporation, which were patterned by lift-off. Platinum served as an ideal adhesion layer on Parylene C. It was chemically inert under physiological conditions but formed strong coordinative bonds with the chlorine substituted onto the Parylene C backbone. The thick layer of malleable gold in the middle of the stack helped amortizing thermal mismatch and other mechanical stresses preventing metal cracking as well as lowering the trace resistance. The top layer of platinum promoted adhesion to the next layer of Parylene C. For this adhesion mechanism to be effective however, it was crucial to achieve low base pressure before the evaporation, ideally on the order of 1·10$^{-8}$ Torr. In order to avoid Parylene craze cracking, it was important to control the chamber and substrate temperature to <100° C.; we achieved highly improved results and stress-free devices with very little curl by switching to an electron-beam evaporator with a cooled chuck.

Lift-off was performed in an acetone bath under agitation with a weak stream of nitrogen for typically 1-2 hours. If lift-off was too slow or incomplete, heating the acetone in a 60° C. water bath could be of help. Sonication or other mechanically assisted methods of lift-off completion were a last resort and should be avoided as they can introduce holes into and bubbles under the Parylene C layer that lead to problems during subsequent vacuum processing steps (etching, metal deposition).

Thick photoresist, SPR-220 (8-12 μm was spun at 1800 RPM) was soft baked at 115° C., exposed using the low-vac mode of Karl Suss MA6 contact-aligner (300 mJ/cm$^2$), post-exposure baked at 115° C. for 390 s, tank-developed for 5-12 min in MF26A developer, and hard-baked at 80° C. for 15 min.

Vias 138, 142, 144 were patterned in the Parylene C by oxygen plasma reactive ion etching (RIE) (oxygen, 200 W, 76 mTorr, 10×30 s intervals with 30 s cool-down periods in Plasma-Therm PK-12 RIE) through an SPR-220 thick (8-12 μm) photoresist mask. The etch rate for Parylene C under these conditions fluctuated around 440 nm min; the etch recipe yielded a sidewall angle of approximately 60°.

Vias, through-holes, and device outlines were etched in identical oxygen plasma etches. While separate masks for vias and outlines may be used, it was realized that metal provides a robust etch stop for oxygen RIE. Hence vias and outlines may be defined on the same mask. This approach cut down on the number of masks needed and helped to clear the vias by a 100% over-etch. After the etch, the remaining PR was stripped in acetone.

Since no adhesion promoter was used before Parylene C deposition onto the silicon carrier wafer 130, a mild detergent bath was sufficient to induce release.

In an optional non-metal configuration, indium tin oxide (ITO) deposition may be used to generate the conductor pattern by lift-off. Indium tin oxide (ITO), a transparent conductor, was successfully spun onto Parylene C. ITO was sputtered from an In$_2$O$_3$: SnO$_2$ (10 wt % SnO$_2$) target in Edwards Auto 306 DC and RF Sputter Coater in argon (Ar) at a pressure of 2.2 mTorr (base pressure: 4·10$^{-5}$ Torr) and a DC power density of 1 W/cm$^2$, yielding a 110 nm thick layer (sputter time: 33 min, deposition rate: 3.3 nm/min).

Additional layer stacking may also be performed. FIG. 7A through FIG. 7J demonstrate device fabrication with up to two conductive layers, interconnected by etched vias. In principle, it is straightforward to extend this process to n conductor layers by repeating steps 112 through 120.

Figure 8:
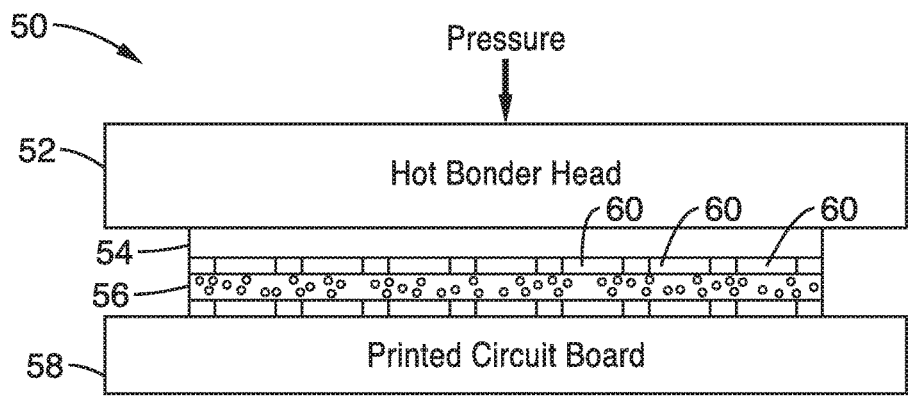
FIG. 8 is a side schematic view during assembly of an integrated IC/antenna shown by anisotropic conductive film (ACF) thermo-compression bonding.
Figure 9A:
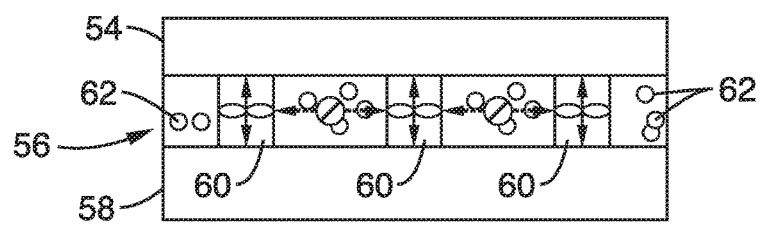
FIG. 9A is an assembled cross-section view of the assembled integrated circuit/antenna of FIG. 8.
Figure 9B:
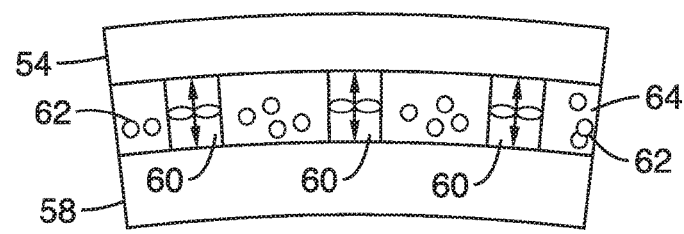
FIG. 9B is a flexed cross-sectional view of the circuit/antenna of FIG. 9A.

In one embodiment shown in FIG. 8 through FIG. 9B, the antenna 26 may be bonded directly to a wireless integrated circuit 58. Contact pads are fabricated through removal of Parylene 54 on the upper-most layer. The integrated circuit 56 is aligned and bonded through flip-chip bonding such as, but not limited to, anisotropic conductive film (ACF) bonding. This process minimizes wiring parasitics and allows compact integration of the full device as shown in FIG. 8 through FIG. 9B.

Referring to the integrated IC/antenna 50 shown in FIG. 8, ACF film 56 having conductive microparticles 62 is thermo-compressed between complementary pad arrays 60. In one embodiment, ACF film 56 (e.g. 3M 5552R, 2 mm wide) was pre-bonded to the PCB 56 using an Ohashi HMB-10 table-top bonder equipped with a 2.5 mm wide bond head 52 (3 s, 90° C., 10 kg/cm$^2$). Parylene cable 54 with bond pads 60 was aligned under a stereomicroscope using a custom alignment system comprising two vacuum chucks mounted on xyz-micropositioners, and tacked to the ACF film with a soldering iron heated to 200° C. The final bond was performed using the HMB-10 (22 s, 200° C., 20 kg/cm$^2$).

Referring to FIG. 9A showing a cross-section of the integrated circuit/antenna, gold-coated polymer microspheres 62 within ACF film 56 establish a robust electrical connection. Between adjacent pads 60, the micro particles 62 remain surrounded by insulating thermoplastic resin (FIG. 9B) that prevents shorts. As shown in the flexed cross-sectional view of FIG. 9B, the ACF resin 64 provides mechanical stability under flexion of all bonds between PCB 58, ACF film 56 and Parylene layer 54.

FIG. 8 through FIG. 9B illustrate a novel implant 50 having monolithic integration of a sub-skin-depth-thin antenna with an ECoG grid on wafer level. A cohesive computational approach was developed to analyze both the power and voltage delivery to the implant 12 under design variations to guarantee efficient and reliable on-chip RF-to-DC conversion.

From the discussion above it will be appreciated that the invention can be embodied in various ways, including but not limited to the following:

1. An apparatus, comprising: a flexible polymer substrate; a thin film antenna; and an array of one or more recording electrodes; wherein the thin film antenna is monolithically integrated with the array of one or more recording electrodes on the flexible polymer substrate to form a conformal monolithic device.

2. An apparatus as in any of the previous embodiments, said monolithic device comprising an implant configured for performing wireless signal acquisition, power delivery, and communication with an external antenna.

3. An apparatus as in any of the previous embodiments, wherein the array of one or more recording electrodes comprises a high-density microfabricated ECoG grid array configured to measure one or more physiological characteristics associated with a patient at an implant site within the patient.

4. An apparatus as in any of the previous embodiments, wherein the thin film antenna comprises a loop antenna disposed around the ECoG grid array.

5. An apparatus as in any of the previous embodiments, wherein the loop antenna is disposed within the same layer as the ECoG grid array.

6. An apparatus as in any of the previous embodiments, wherein the loop antenna and ECoG grid array comprise a nanoscale metallization pattern configured to allow the monolithic device to conform to a non-planar shape of tissue at the implant site.

7. An apparatus as in any of the previous embodiments, wherein the ECoG grid array and loop antenna are disposed within a same wafer level on the flexible polymer substrate.

8. An apparatus as in any of the previous embodiments, wherein the ECoG grid array and loop antenna layer is bonded to an integrated circuit; the integrated circuit configured for executing one or more of said wireless signal acquisition, power delivery, and communication with the external antenna.

9. An apparatus as in any of the previous embodiments, wherein said integrated circuit is bonded as a flip-chip via an anisotropic conductive film thermo-compression.

10. An apparatus as in any of the previous embodiments, wherein ECoG grid array and loop antenna layer comprise a conductive layer having a total thickness of 200 nm.

11. An apparatus as in any of the previous embodiments, wherein said conductive layer comprises a Pt adhesion layer, a ductile Au core, and a biocompatible Pt passivation layer.

12. An implantable device, comprising: a flexible polymer substrate; and an antenna micro-patterned onto the flexible polymer substrate in the form of a polymer thin-film layer; the polymer thin-film layer further comprising an array of one or more recording electrodes configured to measure one or more physiological characteristics associated with a patient at an implant site within the patient.

13. An implantable device as in any of the previous embodiments, wherein the antenna is monolithically integrated with the array of one or more recording electrodes on the flexible polymer substrate to form a conformal application-specific integrated circuit (ASIC).

14. An implantable device as in any of the previous embodiments: said conformal ASIC comprising a monolithic device for performing wireless signal acquisition relating to measurement of the one or more physiological characteristics.

15. An implantable device as in any of the previous embodiments, wherein the polymer thin-film layer is bonded to an integrated circuit; the integrated circuit configured for executing said wireless signal acquisition.

16. An implantable device as in any of the previous embodiments, wherein the integrated circuit is further configured for power delivery and communication with an external antenna.

17. An implantable device as in any of the previous embodiments, wherein the array of one or more recording electrodes comprises a high-density microfabricated ECoG grid array.

18. An implantable device as in any of the previous embodiments, wherein the antenna comprises a loop antenna disposed around the ECoG grid array.

19 An implantable device as in any of the previous embodiments, wherein the loop antenna and ECoG grid array comprise a nanoscale metallization pattern configured to allow the implantable to conform to a non-planar shape of tissue at the implant site.

20. An implantable device as in any of the previous embodiments, wherein the ECoG grid array and loop antenna are disposed within a same wafer level on the flexible polymer substrate.

21. A wireless brain-machine interface (BMI) system, comprising: (a) an external antenna; and (b) an implant, comprising: (i) a flexible polymer substrate; (ii) an antenna micro-patterned onto the flexible polymer substrate in the form of a polymer thin-film layer; (iii) the polymer thin-film layer further comprising a plurality of recording electrodes forming a high-density microfabricated ECoG grid array configured to measure one or more physiological characteristics associated with a patient at an implant site within the patient; (iv) wherein the polymer thin-film layer is bonded to an integrated circuit; (v) the integrated circuit configured for executing one or more of wireless signal acquisition relating to the measurement of the one or more physiological characteristics, power delivery, and communication with the external antenna.

22. A system as in any of the previous embodiments, wherein the antenna comprises a loop antenna disposed around the ECoG grid array.

23 A system as in any of the previous embodiments, wherein the loop antenna and ECoG grid array comprise a nanoscale metallization pattern configured to allow the implantable to conform to a non-planar shape of tissue at the implant site.

24. A system as in any of the previous embodiments, wherein the ECoG grid array and loop antenna are fabricated within a same wafer level fabrication process on the flexible polymer substrate.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims.

Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for." Any element in a claim that does not explicitly state "means for" performing a specified function, is not to be interpreted as a "means" or "step" clause as specified in 35 USC §112, sixth paragraph. In particular, the use of "step of" in the claims herein is not intended to invoke the provisions of 35 USC §112, sixth paragraph.

What is claimed is:
1. An apparatus, comprising:
a flexible polymer substrate;
a thin film antenna; and an array of one or more recording electrodes;
wherein the thin film antenna is monolithically integrated with the array of one or more recording electrodes on the flexible polymer substrate to form a conformal monolithic device;
wherein said monolithic device comprises an implant configured for performing wireless signal acquisition, power delivery, and communication with an external antenna;
wherein the array of one or more recording electrodes comprises a high-density microfabricated ECoG grid array configured to measure one or more physiological characteristics associated with a patient at an implant site within the patient; and
wherein the thin film antenna comprises a loop antenna disposed around the ECoG grid array.

2. An apparatus as recited in claim 1, wherein the loop antenna is disposed within the same layer as the ECoG grid array.

3. An apparatus as recited in claim 2, wherein the ECoG grid array and loop antenna layer is bonded to an integrated circuit;
the integrated circuit configured for executing one or more of said wireless signal acquisition, power delivery, and communication with the external antenna.

4. An apparatus as recited in claim 3, wherein said integrated circuit is bonded as a flip-chip via an anisotropic conductive film thermo-compression.

5. An apparatus as recited in claim 1, wherein the loop antenna and ECoG grid array comprise a nanoscale metallization pattern configured to allow the monolithic device to conform to a non-planar shape of tissue at the implant site.

6. An apparatus as recited in claim 5, wherein the ECoG grid array and loop antenna are disposed within a same wafer level on the flexible polymer substrate.

7. An apparatus as recited in claim 6, wherein ECoG grid array and loop antenna layer comprise a conductive layer having a total thickness of 200 nm.

8. An apparatus as recited in claim 7, wherein said conductive layer comprises a Pt adhesion layer, a ductile Au core, and a biocompatible Pt passivation layer.

9. An implantable device, comprising:
a flexible polymer substrate; and
an antenna micro-patterned onto the flexible polymer substrate in the form of a polymer thin-film layer;
the polymer thin-film layer further comprising an array of one or more recording electrodes configured to measure one or more physiological characteristics associated with a patient at an implant site within the patient;
wherein the array of one or more recording electrodes comprises a high-density microfabricated ECoG grid array; and
wherein the antenna comprises a loop antenna disposed around the ECoG grid array.

10. An implantable device as recited in claim 9, wherein the antenna is monolithically integrated with the array of one or more recording electrodes on the flexible polymer substrate to form a conformal application-specific integrated circuit (ASIC).

11. An implantable device as recited in claim 10;
said conformal ASIC comprising a monolithic device for performing wireless signal acquisition relating to measurement of the one or more physiological characteristics.

12. An implantable device as recited in claim 11, wherein the polymer thin-film layer is bonded to an integrated circuit;
the integrated circuit configured for executing said wireless signal acquisition.

13. An implantable device as recited in claim 12, wherein the integrated circuit is further configured for power delivery and communication with an external antenna.

14. An implantable device as recited in claim 9, wherein the loop antenna and ECoG grid array comprise a nanoscale metallization pattern configured to allow the implantable to conform to a non-planar shape of tissue at the implant site.

15. An implantable device as recited in claim 9, wherein the ECoG grid array and loop antenna are disposed within a same wafer level on the flexible polymer substrate.

16. A wireless brain-machine interface (BMI) system, comprising:
(a) an external antenna; and
(b) an implant, comprising:
(i) a flexible polymer substrate;
(ii) an antenna micro-patterned onto the flexible polymer substrate in the form of a polymer thin-film layer;
(iii) the polymer thin-film layer further comprising a plurality of recording electrodes forming a high-density microfabricated ECoG grid array configured to measure one or more physiological characteristics associated with a patient at an implant site within the patient;
(iv) wherein the polymer thin-film layer is bonded to an integrated circuit;
(v) the integrated circuit configured for executing one or more of wireless signal acquisition relating to the measurement of the one or more physiological characteristics, power delivery, and communication with the external antenna;
(c) wherein the antenna comprises a loop antenna disposed around the ECoG grid array.

17. A system as recited in claim 16, wherein the loop antenna and ECoG grid array comprise a nanoscale metallization pattern configured to allow the implantable to conform to a non-planar shape of tissue at the implant site.

18. A system as recited in claim 16, wherein the ECoG grid array and loop antenna are fabricated within a same wafer level fabrication process on the flexible polymer substrate.

* * * * *